United States Patent
Yang et al.

(10) Patent No.: US 11,534,448 B2
(45) Date of Patent: Dec. 27, 2022

(54) USE OF CANAGLIFLOZIN IN PREPARATION OF ANTITUMOR DRUG

(71) Applicant: ZHEJIANG UNIVERSITY, Hangzhou (CN)

(72) Inventors: Bo Yang, Hangzhou (CN); Qiaojun He, Hangzhou (CN); Ling Ding, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 0 days.

(21) Appl. No.: 16/976,765

(22) PCT Filed: Nov. 4, 2019

(86) PCT No.: PCT/CN2019/115242
§ 371 (c)(1),
(2) Date: Aug. 31, 2020

(87) PCT Pub. No.: WO2020/168741
PCT Pub. Date: Aug. 27, 2020

(65) Prior Publication Data
US 2022/0062316 A1  Mar. 3, 2022

(30) Foreign Application Priority Data
May 13, 2019 (CN) .......................... 201910391746.2

(51) Int. Cl.
*A61K 31/7042* (2006.01)
*A61P 35/00* (2006.01)

(52) U.S. Cl.
CPC .......... *A61K 31/7042* (2013.01); *A61P 35/00* (2018.01)

(58) Field of Classification Search
CPC .. A61K 31/7042; A61K 2300/00; A61P 35/00
See application file for complete search history.

(56) References Cited

U.S. PATENT DOCUMENTS

2013/0281386 A1   10/2013  Anthony et al.
2017/0071970 A1*   3/2017  Rosenthal ............ A61K 31/137

FOREIGN PATENT DOCUMENTS

WO    2016134486 A1   9/2016
WO    2018026673 A1   2/2018

OTHER PUBLICATIONS

EESR(Extend European Search Report) 19912197.1 (dated Apr. 20, 2021).
Villani, L. A. et al. "The diabetes medication Canagliflozin reduces cancer cell proliferation by inhibiting mitochondrial complex-I supported respiration" Dec. 31, 2016.
Shiba, K. et al. "Canagliflozin, an SGLT2 inhibitor, attenuates the development of hepatocellular carcinoma in a mouse model of human NASH" Feb. 5, 2018.

* cited by examiner

*Primary Examiner* — Pancham Bakshi
(74) *Attorney, Agent, or Firm* — W&G Law Group

(57) ABSTRACT

The present invention provides a use of canagliflozin in preparation of an antitumor drug, especially in preparation of a drug for treating solid tumors. It has been proven through researches that canagliflozin has a significant down-regulation effect on immune checkpoint protein PD-L1 in various tumor cells and can effectively enhance the killing effect of T cells on tumor cells in a co-incubation model of T cells and tumor cells, thereby broadening a clinical application scope of the chemical drug canagliflozin in tumor immunotherapy. The present invention provides a new medical use of canagliflozin, and also provides new approaches and potential targets for the development of small molecular drugs based on PD-L1.

3 Claims, 4 Drawing Sheets

Effects of canagliflozin in significantly inhibiting PD-L1 total protein expression in tumor cells Effects of canagliflozin in significantly inhibiting PD-L1 protein expression on surfaces of tumor cells Effects of canagliflozin in significantly promoting PD-L1 protein degradation and shortening a protein half-life thereof Effects of canagliflozin in significantly enhancing killing effect of T cells on tumor cells

USE OF CANAGLIFLOZIN IN PREPARATION OF ANTITUMOR DRUG

CROSS-REFERENCE TO RELATED APPLICATION

This is the United States national phase of International Patent Application No. PCT/CN2019/115242, filed on Nov. 4, 2019, which claims priority to Chinese Patent Application No. 2019103917462, filed on May 13, 2019, the entire contents of each of which are incorporated herein by reference.

TECHNICAL FIELD

The present invention relates to the pharmaceutical field, and particularly, relates to a use of canagliflozin in preparation of an antitumor drug.

BACKGROUND

Programmed death receptor 1 (PD-1) and its ligand (programmed death ligand-1, PD-L1) combine to form an immunosuppressive microenvironment, which plays a pivotal role in tumor immune escape. Several monoclonal antibody drugs that block the PD-1/PD-L1 combining have been successfully applied in the treatment of clinical hematological tumors and solid tumors, and some patients even reach a "clinically cured" status, providing a breakthrough progress in the field of tumor immunotherapy. Although clinical data indicate that PD-1/PD-L1 antibody drugs have significant clinical anti-tumor efficacy, PD-1/PD-L1 monoclonal antibody drugs still face huge challenges. The first challenge is to further enhance a response rate, which is low and is not greater than 20% in the treatment of most solid tumors. Some studies believed that a reason there of may be in that it is difficult for the macromolecular antibody drugs to effectively permeate into tumor tissue to reach all areas of the tumor in a sufficient amount. The second challenge is to further reduce adverse reactions. In the antibody therapy, immune-related adverse events are discrete toxicity caused by non-specific activation of the immune system and may affect almost all organ systems. Compared to the macromolecular antibody drugs, small molecular drugs have advantages such as good permeability in organs or tumors, light stimulation to the immune system, and capability of oral administration. Therefore, an important approach to overcome the defects of antibody drugs is to develop small molecular drugs targeting PD-1/PD-L1, which is also a focus of research in this field.

Currently, the search and development of small molecular drugs targeting PD-1/PD-L1 are mainly conducted based on two concepts: 1) according to characteristics of a crystal structure of the PD-1/PD-L1 complex, developing small molecular drugs with new structures for directly blocking the binding of PD-1 and PD-L1; and 2) based on a protein expression regulation mechanism of PD-L1, designing small molecular compounds to intervene in key processes, in order to inhibit the expression thereof or to promote the degradation thereof. However, most of these compounds are currently still in the laboratory research stage, and the research on the small molecular drugs targeting PD-1/PD-L1 is generally slow.

Currently, canagliflozin is a drug for the clinical treatment of type 2 diabetes mellitus, and its pharmacological mechanism is to inhibit a reabsorption of glucose by inhibiting the activity of sodium-glucose cotransporter 2 (SGLT2) and to promote glucose excretion, so as to achieve the effect of lowering blood sugar level. Canagliflozin is widely used in the treatment of diabetes mellitus because it has a significant hypoglycemic efficacy in hyperglycemic patients and almost has no influence on the normal blood sugar level, and diabetic patients have low risk of hypoglycemia and few adverse reactions when using this type of drugs to lower blood sugar level.

SUMMARY

A purpose of the present invention is to provide a use of canagliflozin in preparation of an antitumor drug, especially in preparation of a drug for treating solid tumors induced by an increased protein level of PD-L1 in tumor cells. A chemical name of canagliflozin is (1S)-1,5-anhydro-1-C-[3-[[5-(4-fluorophenyl)-2-thienyl]methyl]-4-methylphenyl]-D-glucitol, with a molecular formula of $C_{24}H_{25}FO_5S$ and a molecular weight of 444.516.

It was found and substantiated through in-vitro assays using Western blotting and flow cytometry that canagliflozin (20 µM) significantly lowered the expressions of immune checkpoint protein PD-L1 and cell surface PD-L1 in non-small cell lung cancer cells and osteosarcoma cells. In addition, in a co-incubation model of T cells and tumor cells, canagliflozin can effectively enhance a killing effect of T cells on tumor cells, which was similar to that of a positive control PD-L1 antibody drug.

The drug is prepared with canagliflozin and pharmaceutically acceptable excipients, and is in a formulation of gel, soft capsule, oral preparation, injection solution, lyophilized powder for injection, or infusion solution. The drug is administrated once a day.

Canagliflozin is an activity inhibitor of sodium-glucose cotransporter 2 (SGLT2), and is mainly used for the current clinical treatment of type 2 diabetes mellitus. The present invention has proven by in-vitro assays that canagliflozin has a significant down-regulation effect on the immune checkpoint protein PD-L1 in various tumor cells, and can effectively enhance the killing effect of T cells on tumor cells in the co-incubation model of T cells and tumor cells, thereby broadening a clinical application scope of the chemical drug canagliflozin in tumor immunotherapy. The present invention not only provides possibilities of applying canagliflozin in the clinical tumor treatments, but also provides new approaches and potential targets for the development of small molecular drugs based on PD-L1.

The applicants previously conducted a systematic screening of drugs for clinical uses and found that canagliflozin, used for clinical treatment of type 2 diabetes mellitus, can significantly lower the PD-L1 protein level in various tumor cells and restore the killing effect of T cells on tumor cells. There are no clinically available small molecular inhibitors which achieve the antitumor efficacy by intervening in the protein expression regulation mechanism of PD-L1. Meanwhile, there are no published researches on the regulation of PD-L1 protein expression with canagliflozin. The present invention uses the existing small molecular inhibitor for tumor immunotherapy, and provides new medical uses for canagliflozin.

DESCRIPTION OF EMBODIMENTS

The present invention is further described with reference to the drawings in combination with examples.

Example 1

Effects of canagliflozin in significantly down-regulating PD-L1 protein level after effecting on the non-small cell lung cancer H1299 cells and the osteosarcoma MG63 cells for 24 h. The specific procedures are described below.

Figure 1:
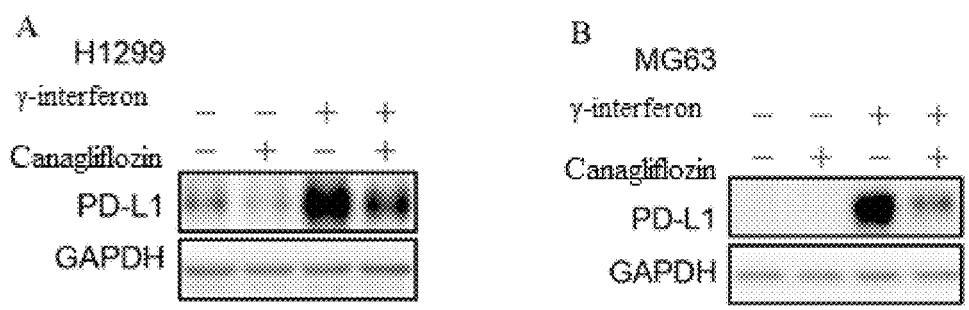
FIG. 1 illustrates Western blotting images of canagliflozin (20 µM) on non-small cell lung cancer H1299 cells and osteosarcoma MG63 cells.

Multiple human tumor cells, non-small cell lung cancer H1299 cells and osteosarcoma MG63 cells, were selected and respectively inoculated in 6-well plates ($1.0 \times 10^6$ cells/well), and incubated overnight in incubator at 37° C. with 5% $CO_2$. On the next day, each plate was added with canagliflozin (20 μM) and γ-interferon (IFNγ, 10 ng/mL), and after 24 hours, the cells were collected and lysed to extract the proteins. The expression of PD-L1 in the cells were detected by Western blotting. The inhibitory effects of canagliflozin on the PD-L1 protein in the non-small cell lung cancer H1299 cells and the osteosarcoma MG63 cells are illustrated in FIG. 1, showing that canagliflozin significantly inhibited the PD-L1 total protein expression in the tumor cells.

Example 2

Effects of canagliflozin in significantly down-regulating PD-L1 protein level on cell membrane surface after effecting on the non-small cell lung cancer H1299 cells and the osteosarcoma MG63 cells for 24 h. The specific procedures are described below.

Figure 2:
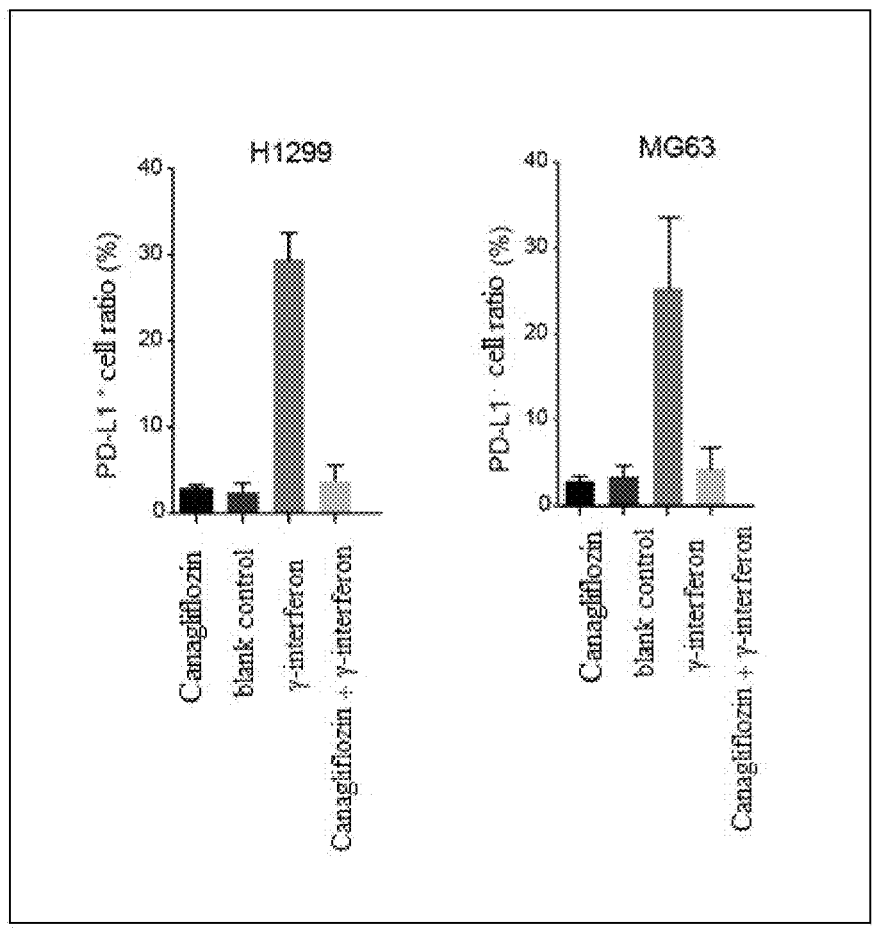
FIG. 2 illustrates flow cytometry histograms of canagliflozin (20 μM) on non-small cell lung cancer H1299 cells and osteosarcoma MG63 cells.

Two human tumor cell lines, non-small cell lung cancer H1299 cells and osteosarcoma MG63 cells, were selected and respectively inoculated in 6-well plates ($1.0 \times 10^6$ cells/well), and incubated overnight in incubator at 37° C. with 5% $CO_2$. On the next day, each plate was added with canagliflozin (20 μM) and γ-interferon (IFNγ, 10 ng/mL), and after 24 hours, the PD-L1 expressions on the cell surfaces were detected with flow cytometry. The specific inhibitory effects of canagliflozin on the PD-L1 protein in the non-small cell lung cancer H1299 cells and the osteosarcoma MG63 cells are illustrated in FIG. 2, showing that canagliflozin significantly inhibited the PD-L1 protein expression on the tumor cell surfaces.

Example 3

Effects of canagliflozin on the stability of the PD-L1 protein in the non-small cell lung cancer H1299 cells. The specific procedures are described below.

Figure 3:
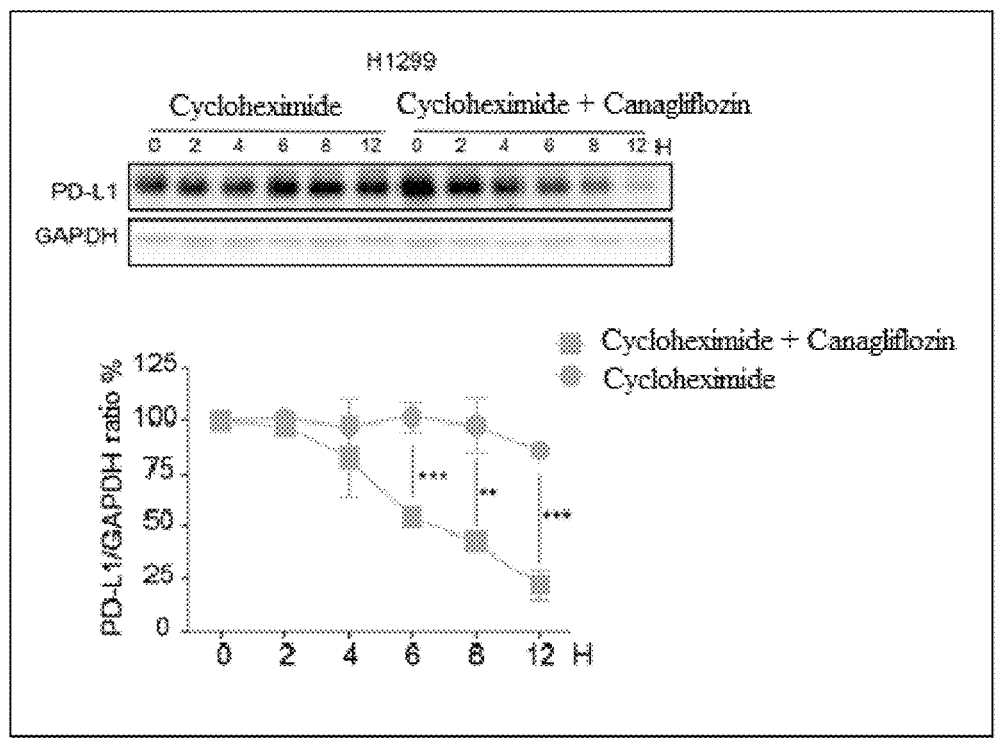
FIG. 3 illustrates influences of canagliflozin (20 μM) on a stability of PD-L1 protein in non-small cell lung cancer H1299 cells.

The non-small cell lung cancer H1299 cells were inoculated in 6-well plates ($1.0 \times 10^6$ cells/well), and incubated overnight in incubator at 37° C. with 5% $CO_2$. On the next day, the plates were first added with γ-interferon (IFNγ, 10 ng/mL), and after 24 hours, a protein synthesis inhibitor cycloheximide (CHX, 10 g/mL) or a co-administration group of CHX (10 g/mL)+canagliflozin (20 μM) was administrated simultaneously for these plates. After 0 h, 2 h, 4 h, 6 h, 8 h, and 12 h, respectively, the cells were collected to detect the change of the protein level of PD-L1 in the cells by Western blotting, and a gray-scale analysis was performed to plot a curve for investigating the protein stability. As shown in FIG. 3, canagliflozin significantly promoted the degradation of the PD-L1 protein and shortened a half-life of the PD-L1 protein.

Example 4

Effects of canagliflozin in enhancing the killing effects of T cells on the non-small cell lung cancer H1299 cells and the osteosarcoma MG63 cells. The specific procedures are described below.

Figure 4:
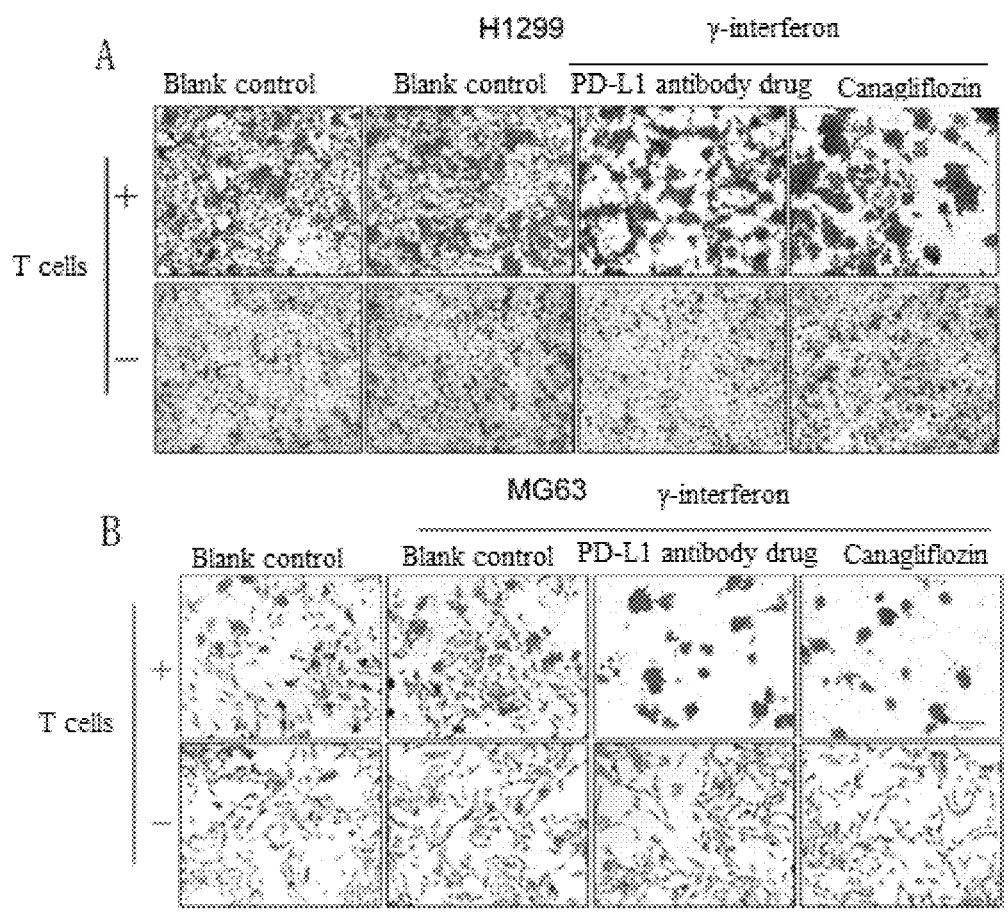
FIG. 4 illustrates that canagliflozin (20 μM) enhances the killing effect of T cells on non-small cell lung cancer H1299 cells and osteosarcoma MG63 cells.

PBMC cells were isolated from human blood samples using Ficoll separation solution, and then stimulated with CD3 and CD28 for 3 days to activate T cells in PBMC, and in the meantime, interleukin-2 (IL-2, 50 U/uL) was administrated to maintain the growth of T cells. The activated T cells were co-incubated with the tumor cells that had been treated with canagliflozin (20 μM) and γ-interferon (IFNγ, 10 ng/mL) for 24 hours. A PD-L1 antibody drug was used as a positive control. The killing effect of T cells on tumor cells was investigated, and a crystal violet staining method was employed to investigate the killing effect of T cells on tumor cells. The specific results are shown in FIG. 4, showing that canagliflozin significantly enhanced the killing effect of T cells on tumor cells.

What is claimed is:

1. A process for treating a tumor, comprising administrating a composition into a subject suffering from a tumor,
    wherein the composition consists of canagliflozin and a pharmaceutically acceptable excipient, and the canagliflozin is (1S)-1,5-anhydro-1-C-[3-[[5-(4-fluorophenyl)-2-thienyl]methyl]-4-methylphenyl]-D-glucitol,
    with a molecular formula of and a molecular $C_{24}H_{25}FO_5S$ weight of 444.516;
    wherein the tumor is non-small cell lung cancer and osteosarcoma.

2. The process according to claim 1, wherein the tumor is induced by an increased PD-L1 protein level in tumor cells.

3. The process according to claim 1, wherein the composition is provided in a formulation of gel, soft capsule, oral preparation, injection solution, lyophilized powder for injection, or infusion solution.

* * * * *